US008183530B2

(12) United States Patent
Falen et al.

(10) Patent No.: US 8,183,530 B2
(45) Date of Patent: May 22, 2012

(54) POSITRON EMISSION TOMOGRAPHY AND OPTICAL TISSUE IMAGING

(75) Inventors: Steven W. Falen, Carmichael, CA (US); Richard A. Hoefer, Newport News, VA (US); Stanislaw Majewski, Yorktown, VA (US); John McKisson, Hampton, VA (US); Brian Kross, Yorktown, VA (US); James Proffitt, Newport News, VA (US); Alexander Stolin, Newport News, VA (US); Andrew G. Weisenberger, Yorktown, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 121 days.

(21) Appl. No.: 12/319,649

(22) Filed: Jan. 9, 2009

(65) Prior Publication Data

US 2011/0089326 A1    Apr. 21, 2011

(51) Int. Cl.
*G01T 1/166* (2006.01)

(52) U.S. Cl. .................................................. 250/363.03
(58) Field of Classification Search .............. 250/363.03
See application file for complete search history.

(56) References Cited

U.S. PATENT DOCUMENTS

| 4,057,727 | A | * | 11/1977 | Muehllehner et al. ... | 250/363.03 |
| 5,252,830 | A | * | 10/1993 | Weinberg ................. | 250/363.02 |
| 2008/0161672 | A1 | * | 7/2008 | Marar ..................... | 600/407 |
| 2009/0015826 | A1 | * | 1/2009 | Ramanujam et al. ..... | 356/244 |
| 2010/0121172 | A1 | * | 5/2010 | Ladic et al. .............. | 600/407 |

* cited by examiner

*Primary Examiner* — Constantine Hannaher

(57) ABSTRACT

A mobile compact imaging system that combines both PET imaging and optical imaging into a single system which can be located in the operating room (OR) and provides faster feedback to determine if a tumor has been fully resected and if there are adequate surgical margins. While final confirmation is obtained from the pathology lab, such a device can reduce the total time necessary for the procedure and the number of iterations required to achieve satisfactory resection of a tumor with good margins.

1 Claim, 2 Drawing Sheets

POSITRON EMISSION TOMOGRAPHY AND OPTICAL TISSUE IMAGING

The United States of America may have certain rights to this invention under Management and Operating Contract DE-AC05-06OR23177 from the United States Department of Energy.

FIELD OF THE INVENTION

The present invention relates to positron emission tomography (PET) imaging and more particularly to a combined PET and optical imaging system for the rapid determination of adequate cancerous tissue resection and surgical margins during surgical procedures for the removal of cancerous tissue.

BACKGROUND OF THE INVENTION

During cancer surgeries, one of the important concerns is to determine if there are satisfactory surgical margins around the cancerous tissue. Ideally, the surgeon would like to remove all of the tumor, with adequate margins around the cancerous tissue, but without taking out too much of the healthy surrounding tissue. Typically, after the lesion is surgically removed, the tissue is sent to a pathology lab to determine if the margins around the cancer are sufficient. This process can take 20-30 minutes or more to get a confirmation that the tumor has been excised and that there are adequate surgical margins. During that time, the surgeon(s) must wait for confirmation. If the margins are not adequate, this process may be repeated several times before the surgery is concluded, adding substantial idle time to the surgery. For the patient, the time lost during this process results in increased time in surgery and extended exposure to anesthesia, which can result in increased morbidity. Increased surgical time can also lead to overall increased costs for the procedure.

It would therefore be highly desirable to have a method and apparatus for rapidly determining if adequate cancerous tissue resection has been made and adequate surgical margins allowed during surgical procedures for the removal of cancerous tissue.

OBJECT OF THE INVENTION

It is therefore an object of the present invention to provide a method and apparatus for the rapid determination of the boundaries of cancerous tissue and the determination of the presence of adequate margins thereabout after resection during surgery.

SUMMARY OF THE INVENTION

According to the present invention there is provided a mobile compact imaging system that combines both PET and optical imaging into a single system which can be located in the operating room (OR) and provides faster feedback to determine if a tumor has been fully resected and if there are adequate surgical margins. While the final confirmation is obtained from the pathology lab, such a device can reduce the total time necessary for the procedure and the number of iterations required to achieve satisfactory resection of a tumor with good margins.

DETAILED DESCRIPTION

Figure 1:
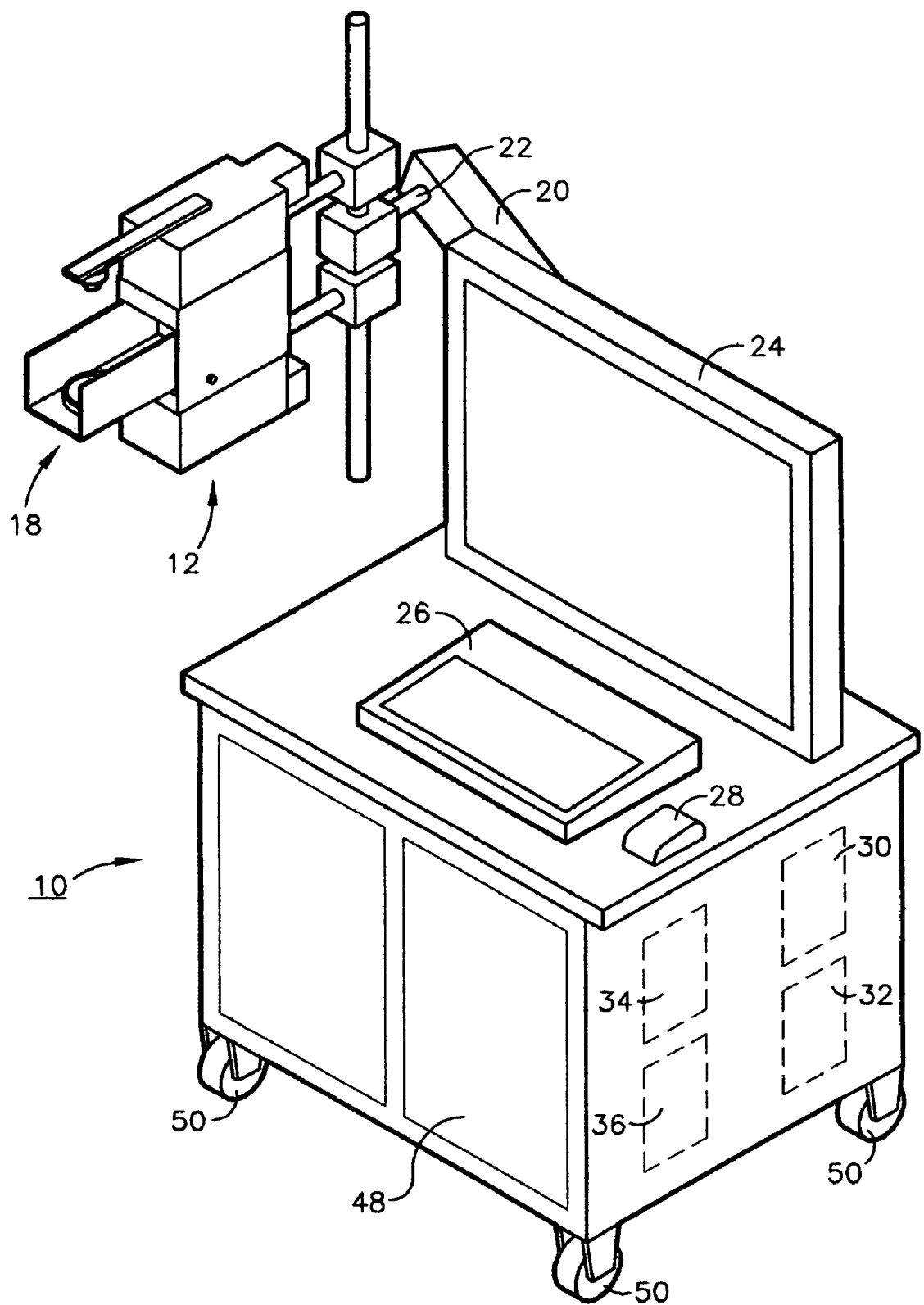
FIG. 1 is a partially phantom perspective view of the imaging system of the present invention.

Positron Emission Tomography with F-18 fluoro-deoxy-glucose (FDG) has been shown to be a valuable tool for imaging various cancers. Many cancers demonstrate increased glucose metabolism compared to normal tissues. When FDG is injected intravenously, it concentrates in tumors allowing them to be imaged. In the protocol used in connection with the imaging system of the present invention, one hour before surgery, the patient is injected with a small amount of a positron emitting radiopharmaceutical such as FDG. When the surgeon has removed the cancerous lesion, he or she will mark the resected tissue and the surgical bed with dyes to map orientation for analysis of margins.

The Positron Emission Tomography (PET) Tissue Sample Imager of the present invention uses a pair of small PET cameras to image radiotracer uptake in the resected tissue sample. The cancerous tissue will typically be identified as a focal area or areas of increased radiotracer accumulation within the sample. The PET Tissue Sample Imager of the present invention also allows for obtaining a co-registered optical image of the tissue sample. The metabolic PET image demonstrating radiotracer accumulation is fused onto the optical image for display. Evaluating the fused images in two different 90° orientations allows the surgeon to determine if there are adequate margins of normal tissue around the tumor or if further intervention is required. This approach also allows the surgeon to observe the physical location of tissue within the patient by observation of the optical image. This process can be completed in just a few minutes in the operating room thus eliminating the need for iterative pathological examinations.

Referring now to the accompanying drawings, the dual-modality, mobile imager of the present invention 10 comprises:

1) a planar PET imager 12 that typically, but not necessarily, exhibits a 10 cm×20 cm field of view and ~1.5-3.0 mm planar reconstruction resolution;
2) a PET module mounting and co-registration fixture with sample-tray guides 14;
3) an optical camera 16;
4) a tissue sample tray 18;
5) a mobile gantry compatible with an operating room environment 20;
6) an optional arm with PET imager mount 22;
7) a computer 34 with monitor 24, keyboard 26 and mouse 28;
8) imager electronics with low voltage and high voltage power supplies 30;
9) a PET module data acquisition system 32;
10) data acquisition and processing software loaded on computer 34;
11) image fusion software loaded on computer 34; and
12) a UPS/isolation transformer 36.

Several PET imaging technologies can be implemented in planar PET imager 12 of the present invention. The preferred general type of apparatus will have a scintillator as a sensor/energy converter of the 511 keV annihilation gamma rays, while different photodetectors will serve as detectors of the scintillation light produced by the absorbed 511 keV gamma rays in the scintillator gamma sensor. The scintillator sensor can be made of pixellated or plate crystal scintillator materials such as LSO, LYSO, GSO, BGO, LaBr3, NaI(Tl), CsI(Tl), CsI(Na), and others. The photodetector may comprise a standard or multi-element photomultiplier, position sensitive, flat panel or microchannel plate based photomultiplier, an avalanche photodiode array or large size avalanche photodiodes with resistive etc. readout, or different variants of the novel so-called Silicon photomultiplier.

Examples of preferred PET imager technologies include, but are not limited to:

1) imagers based on two opposed detector heads 12A and 12B, each made with an array of 2" Hamamatsu Flat Panel Position Sensitive Photomultipliers (PSPMTs) coupled to an array of 2 mm×2 mm×15 mm LYSO scintillators and forming a planar PET imager with a ~JO cm×10 cm active field of view;
2) for a more compact, lighter implementation, the PSPMTs can be replaced with Silicon PMTs such as those available from SensL, of Mountain View, Calif.;
3) other PET isotope compatible detector technology such as position sensitive APDs and solid state detector material such as cadmium zinc telluride;
4) similar fast on-board readout and multi-channel data acquisition systems can also be used.

A prototype of the tissue sample imaging system of the present invention was built and tested in a laboratory environment. The imager was implemented on a modified mobile gantry equipped with an articulating arm initially designed by for a thyroid uptake probe. The system was adapted to include the following elements: an electronics cabinet housing electronics, power supplies, and cabling; a shelf housing computer and data acquisition box; ~medical quality UPS/isolation transformer to assure uninterrupted power during surgery and to provide an electrical safety buffer; a compact computer; and a medical quality touch screen monitor for ease of operation and cleaner environment (in principle no keyboard use is needed).

Figure 2:
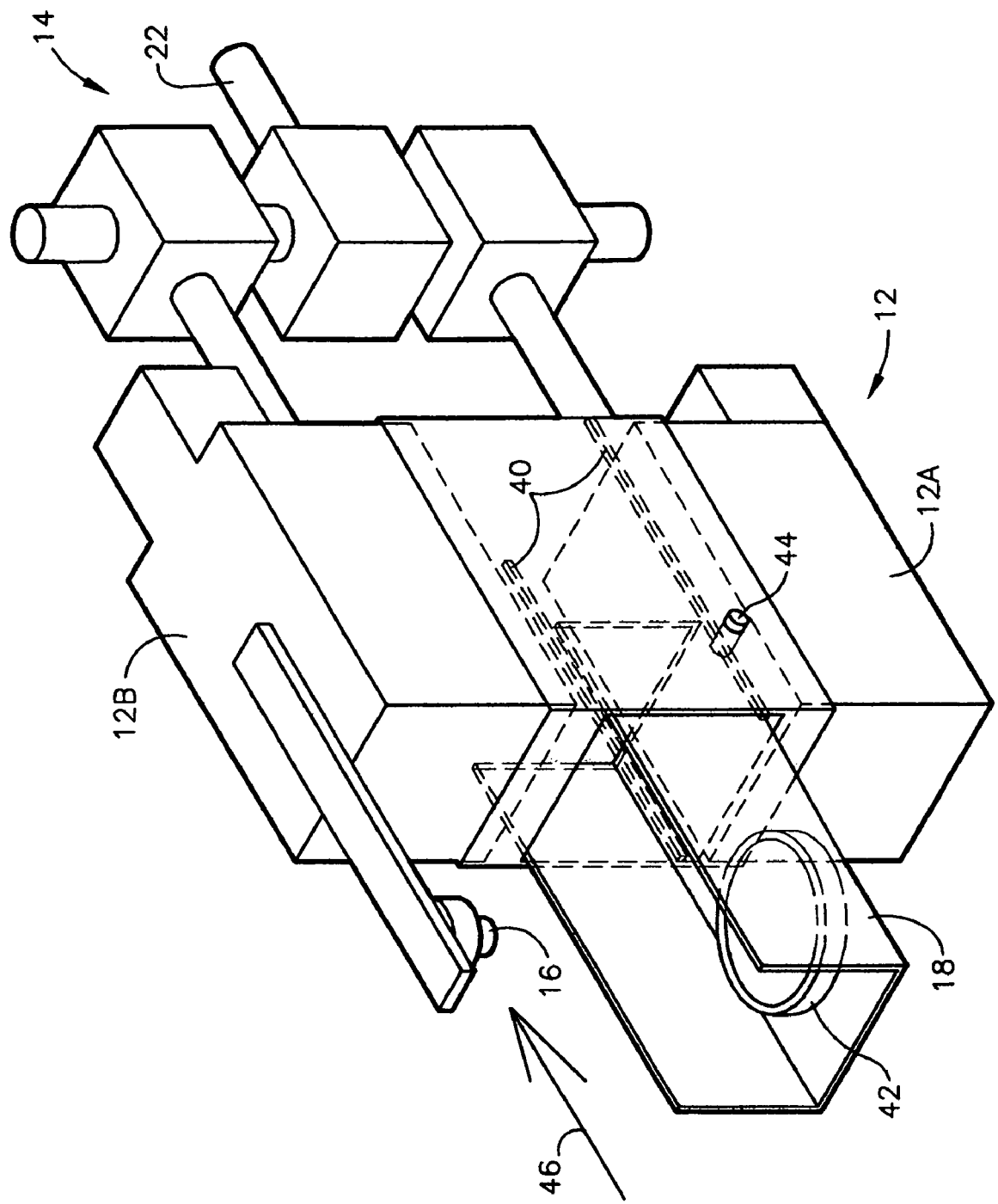
FIG. 2 is a partially phantom perspective view of the module mounting and co-registration fixture with sample-tray guides of the imaging system of the present invention.

As depicted in FIG. 2, an important feature of this imaging device 10 of the present invention is a sample tray 18 including a sample holder 42 that aligns the two imagers/cameras 12 and 16 by means of a pair of rails 40 that guide sample holder 42 position based on PET imager 12 location. This device ensures that PET imagers 12A and 12B are parallel and separated by the appropriate distance. Sample-tray 14 contains sample holder 42 that is preferably a radiolucent Petri dish that holds the tissue sample. This tray moves in rails 40 on the inside of sample holder 14. A stop-pin 44 positions tissue sample holder 42 under optical camera 16 where a digital photograph is taken. After the optical image is acquired, stop pin 44 is backed out which allows sample-tray 14 to be translated in the direction shown by arrow 46 to a central position in PET imager 12 where the PET image is acquired. The PET image is then merged with the optical image and displayed on touch screen monitor 24.

Mounting of imaging system 10 on/in a cart 48 that includes casters or wheels 50 allows for movement of imaging system 10 into, out and within the operating room.

There has thus been described a mobile compact imaging system that is located in the operating room (OR) which imaging system provides faster feedback to determine if a tumor has been fully resected and if there are adequate surgical margins.

As the invention has been described, it will be apparent to those skilled in the art that the same may be varied in many ways without departing from the intended spirit and scope of the invention, and any and all such modifications are intended to be included within the scope of the appended claims.

What is claimed is:

1. A compact mobile imaging system comprising:
   A) a positron emission tomography imager;
   B) an optical imager; and
   C) a computer; said computer having positron emission tomography data acquisition software, digital optical imaging software, and positron emission tomography image and digital optical image fusion software;
all mounted on a moveable cart and including a sample holder for retaining a sample of tissue for bimodal overlapping imaging; said sample holder comprising:
   a) a radiolucent Petri dish that holds a sample for imaging;
   b) rails on the inside of the sample holder, and
   c) a removable stop pin in the sample holder that positions the radiolucent Petri dish in the rails for alternately imaging under the optical imager for optical digital imaging and imaging under the PET imager for PET imaging,
wherein the moveable stop pin can be removed after optical imaging and the sample holder translated to a position for overlapping of the imaging system of imaging.

* * * * *